US012758084B2

(12) United States Patent
Oyama

(10) Patent No.: US 12,758,084 B2
(45) Date of Patent: Oct. 13, 2026

(54) ENDOSCOPE, INSERTION PORTION OF ENDOSCOPE, AND METHOD FOR MANUFACTURING INSERTION PORTION

(71) Applicant: OLYMPUS CORPORATION, Tokyo (JP)

(72) Inventor: Katsumi Oyama, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 674 days.

(21) Appl. No.: 17/726,017

(22) Filed: Apr. 21, 2022

(65) Prior Publication Data

US 2022/0240752 A1 Aug. 4, 2022

Related U.S. Application Data

(63) Continuation of application No. PCT/JP2019/042226, filed on Oct. 28, 2019.

(51) Int. Cl.
*A61B 1/00* (2006.01)
*A61B 1/005* (2006.01)

(52) U.S. Cl.
CPC ............ *A61B 1/0011* (2013.01); *A61B 1/005* (2013.01)

(58) Field of Classification Search
CPC ... A61B 1/0011; A61B 1/0055; A61B 1/0056; A61B 2017/00309; A61M 25/0009;
(Continued)

(56) References Cited

U.S. PATENT DOCUMENTS 4,347,837 A * 9/1982 Hosono .............. G02B 23/2476
356/241.4
2002/0016525 A1* 2/2002 Ishibiki .............. A61B 1/00071
600/133

(Continued)

FOREIGN PATENT DOCUMENTS

CN 202505311 U 10/2012
JP H06-285010 A 10/1994

(Continued)

OTHER PUBLICATIONS

Arkema Canada Inc., Material Safety Data Sheet PEBAX, Sep. 27, 2005, Arkema Canada Inc., pp. 1-3. (Year: 2005).*

(Continued)

*Primary Examiner* — Michael J Carey
*Assistant Examiner* — Stephen Floyd London
(74) *Attorney, Agent, or Firm* — Scully, Scott, Murphy & Presser, P.C.

(57) ABSTRACT

An endoscope includes: an insertion portion formed using a first resin material and having a fusion surface, the first resin material having a melting point of a first temperature; a bending portion formed using a second resin material having a melting point of a second temperature higher than the first temperature, the bending portion being interposed in the insertion portion at a predetermined position and being bendable in a predetermined direction; and an elastic member formed into a tubular shape by using a third resin material different from the first resin material, the elastic member being configured to cover the bending portion, an end portion of the elastic member being fused to the fusion surface.

19 Claims, 3 Drawing Sheets

(58) Field of Classification Search
CPC ............ A61M 25/001; A61M 25/0012; A61M 25/0013; A61M 25/0014; A61M 25/0015; A61M 25/0138; A61M 2025/0188
See application file for complete search history.

(56) References Cited

U.S. PATENT DOCUMENTS

| | | | | |
|---|---|---|---|---|
| 2003/0216616 | A1* | 11/2003 | Krupa | A61B 1/0055 600/920 |
| 2005/0171591 | A1* | 8/2005 | McHale | A61M 25/0052 606/191 |
| 2006/0258911 | A1* | 11/2006 | Sato | A61B 1/00117 600/920 |
| 2009/0093680 | A1* | 4/2009 | Tsutsumi | A61B 1/0008 600/140 |
| 2009/0253963 | A1* | 10/2009 | Suigetsu | A61B 1/0055 425/446 |
| 2010/0249511 | A1* | 9/2010 | Miyagi | A61B 1/0011 600/139 |
| 2012/0215068 | A1* | 8/2012 | Furuta | A61B 1/0051 600/125 |
| 2013/0304035 | A1* | 11/2013 | Cabiri | A61B 17/00234 604/528 |
| 2014/0135736 | A1* | 5/2014 | Hebert | A61M 25/0147 604/525 |
| 2016/0007832 | A1* | 1/2016 | Shimada | A61B 1/0125 604/95.04 |
| 2016/0278617 | A1* | 9/2016 | Okaniwa | A61B 1/0052 |
| 2020/0070482 | A1* | 3/2020 | Attinger | B32B 27/36 |

FOREIGN PATENT DOCUMENTS

| | | | |
|---|---|---|---|
| JP | H09-108175 | A | 4/1997 |
| JP | H09299319 | A | * 11/1997 |
| JP | H10-94514 | A | 4/1998 |
| JP | 2000-041937 | A | 2/2000 |
| JP | 2006-167309 | A | 6/2006 |
| JP | 2007-159854 | A | 6/2007 |
| JP | 2012-170628 | A | 9/2012 |
| JP | 2014-030659 | A | 2/2014 |

OTHER PUBLICATIONS

PolymPart, PES poly(ether sulfone), Sep. 20, 2024 [retrieved on Sep. 20, 2024]. Retrieved from internet <URL:http://www.download.polympart.ir/polympart/PolymerReference/PES%20-%20poly-ether-sulfone.pdf>. (Year: 2024).*

Wanhua Chemical Netherlands, Safety Data Sheet (SDS) WHT-1185EC, Nov. 6, 20215, Version 1.0, pp. 1-7 (Year: 2015).*

International Search Report dated Dec. 17, 2019 received in PCT/JP2019/042226.

* cited by examiner

ENDOSCOPE, INSERTION PORTION OF ENDOSCOPE, AND METHOD FOR MANUFACTURING INSERTION PORTION

CROSS REFERENCE TO RELATED APPLICATION

This application is a continuation application of PCT/JP2019/042226 filed on Oct. 28, 2019, the entire contents of which are incorporated herein by this reference.

BACKGROUND OF THE INVENTION

1. Field of the Invention

The present invention relates to an endoscope including a bending portion covered by an elastic member, to an insertion portion of an endoscope, and to a method for manufacturing an insertion portion.

2. Description of the Related Art

As disclosed in Japanese Patent Application Laid-Open Publication No. 2007-159854, for example, an endoscope used for medical purpose, for example, has a configuration where an insertion portion is covered by a tubular member so as to maintain watertightness of the insertion portion. Japanese Patent Application Laid-Open Publication No. 2007-159854 discloses a technique where a rigid portion provided on a distal end of the insertion portion is formed using a thermoplastic resin, and an outer skin made of a thermoplastic resin is fused to the rigid portion to cover the insertion portion by the outer skin.

Further, as a method for manufacturing an endoscope at low cost by reducing the number of parts used for forming the insertion portion, a technique is known where a bending portion is formed using a resin.

SUMMARY OF THE INVENTION

One aspect of the present invention is directed to an endoscope including: an insertion portion formed using a first resin material and having a fusion surface, the first resin material having a melting point of a first temperature; a bending portion formed using a second resin material having a melting point of a second temperature higher than the first temperature, the bending portion being interposed in the insertion portion at a predetermined position and being bendable in a predetermined direction; and an elastic member formed into a tubular shape using a third resin material different from the first resin material, the elastic member being configured to cover the bending portion, an end portion of the elastic member being fused to the fusion surface.

Another aspect of the present invention is directed to an endoscope including: an insertion portion formed using a first resin material and having a fusion surface, the first resin material having a melting point of a first temperature; a bending portion formed using a second resin material having a melting point of a second temperature higher than the first temperature, the bending portion being interposed in the insertion portion at a predetermined position and being bendable in a predetermined direction; an elastic member being a tubular member having a first end and a second end and made of a resin, the elastic member being configured to cover the bending portion; and a distal end forming portion forming a distal end portion of the insertion portion, and integrally formed with the first end of the elastic member, wherein the second end of the elastic member is fused to the fusion surface.

Yet another aspect of the present invention is directed to an insertion portion of an endoscope, the insertion portion including: a distal end forming portion formed using a first resin material having a melting point of a first temperature; a bending portion formed using a second resin material having a melting point of a second temperature higher than the first temperature, the bending portion being continuously provided on a proximal end side of the distal end forming portion; an elastic member being a tubular member having a first end and a second end and covering the bending portion, the elastic member being formed using a third resin material different from the first resin material and having a melting point of a third temperature, the first end being fused to the distal end forming portion; and a flexible tube continuously provided on a proximal end side of the bending portion.

Yet another aspect of the present invention is directed to a method for manufacturing an insertion portion of an endoscope, the method including: forming a distal end forming portion from a first resin material having a melting point of a first temperature; forming a bending portion using a second resin material having a melting point of a second temperature higher than the first temperature, and causing the bending portion to be continuously provided on a proximal end side of the distal end forming portion; causing a flexible tube to be continuously provided on a proximal end side of the bending portion; and forming an elastic member from a tubular member having a first end and a second end and causing the first end of the elastic member to be fused to the distal end forming portion, the elastic member being formed using a third resin material having a melting point of a third temperature and being different from the first resin material.

DETAILED DESCRIPTION OF THE PREFERRED EMBODIMENTS

Figure 1:
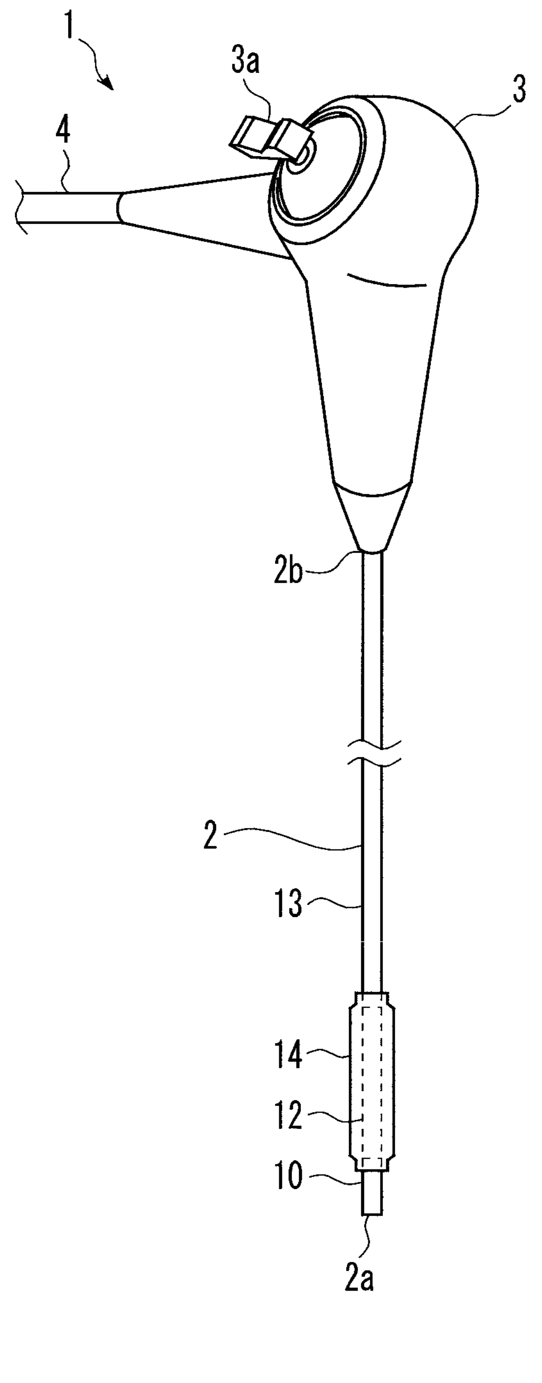
FIG. 1 is a view showing a schematic configuration of an endoscope of a first embodiment.

Hereinafter, preferred modes of the present invention will be described with reference to drawings. In respective drawings used in the description made hereinafter, to allow respective constituent elements to have sizes which are visible in the drawings, each constituent element may have a different scale, and the present invention is not limited to the number of constituent elements, the shape of the constituent elements, size ratios of the constituent elements, or relative positional relationships between the respective constituent elements described in these drawings.

First Embodiment

FIG. 1 is a view schematically showing a configuration of an endoscope 1 of the present embodiment. The endoscope 1 includes an insertion portion 2, an operation portion 3, and a connection cable 4. The insertion portion 2 has an elongated shape and is inserted into a subject. The operation portion 3 is connected with a proximal end 2*b* of the insertion portion 2. The connection cable 4 extends from the operation portion 3. A subject into which the insertion portion 2 is inserted may be a living subject, such as a person, or may be a non-living subject, such as a machine or a building.

Figure 2:
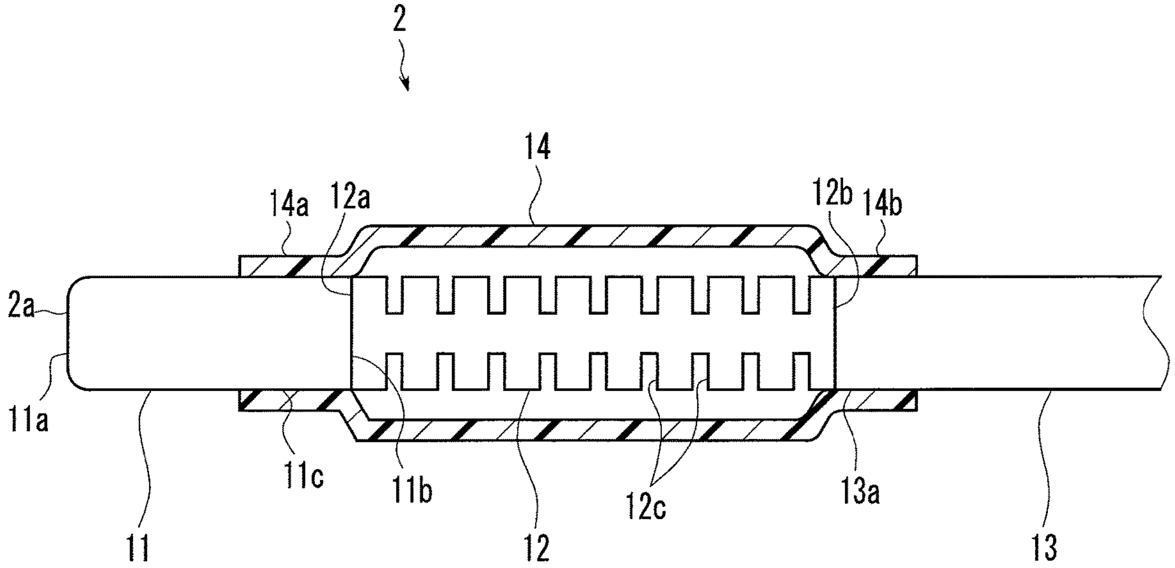
FIG. 2 is a partial cross-sectional view of an insertion portion of the first embodiment.

As shown in FIG. 2, the insertion portion 2 is formed by continuously connecting a distal end forming portion 11, a bending portion 12, and a flexible tube 13 in this order from a distal end 2*a* toward the proximal end 2*b*. The bending portion 12 is covered by a tubular elastic member 14. FIG. 2 is a partial cross-sectional view of the elastic member 14 taken along a plane including a center axis of the insertion portion 2 to allow the distal end forming portion 11, the bending portion 12, and the flexible tube 13 to be easily recognized.

Facing FIG. 2, a lateral direction corresponds to a longitudinal direction of the insertion portion 2. A left side in FIG. 2 is a distal end 2*a* side of the insertion portion 2, and a right side in FIG. 2 is a proximal end 2*b* side of the insertion portion 2.

The distal end forming portion 11 is provided with an image pickup apparatus not shown in the drawing. The image pickup apparatus includes an image sensor (imager), an objective lens, and the like. The distal end forming portion 11 is also provided with an illumination window not shown in the drawing. Illumination light for illuminating an object for the image pickup apparatus is emitted from the illumination window.

The connection cable 4 includes a connector connected to a processor being an external device. The endoscope 1 has a so-called video scope mode, and an image picked up by the image pickup apparatus is displayed on an image display device connected to the processor. A light source of illumination light may be provided in the distal end forming portion 11, or may be provided in the processor. The image pickup apparatus and the illumination window, which are provided in the distal end forming portion 11, have known configurations and hence, detailed description of such configurations will be omitted.

The distal end forming portion 11 is a columnar member extending in the longitudinal direction of the insertion portion 2. A space is formed in the distal end forming portion 11, and the above-mentioned image pickup apparatus, illumination window, and the like are held in the space. In other words, the distal end forming portion 11 is a frame-like member that holds internal components, such as the image pickup apparatus and the illumination window, at predetermined positions near the distal end 2*a* of the insertion portion 2. The internal component may include a conduit or an electronic component.

The distal end forming portion 11 may be formed of a single member, or may be formed by combining a plurality of members. The distal end forming portion 11 has a fusion surface 11*c* at least at a portion of an outer peripheral surface. The fusion surface 11*c* is formed using a first material being a thermoplastic resin. On the outer peripheral surface of the distal end forming portion 11, the fusion surface 11*c* has at least a predetermined width in the longitudinal direction of the insertion portion 2, and is disposed over the entire region in a circumferential direction. A melting point of the first material is a first temperature T1.

In the present embodiment, for example, the distal end forming portion 11 is a single member formed using the first material being a resin. The distal end forming portion 11 is a resin molded product formed using the first material. Accordingly, in the present embodiment, the entire outer peripheral surface of the distal end forming portion 11 is the fusion surface 11*c*.

The first material is so-called engineering plastic. It is sufficient for the first material to satisfy conditions that relate to physical properties of a material used for forming the bending portion 12 and the elastic member 14 described later, but a kind of the first material is not particularly limited.

In the present embodiment, for example, the first material is polycarbonate (PC). In a case where the first material is polycarbonate, the first temperature T1 being the melting point is approximately 160° C.

Note that the first material may be a styrene butadiene acrylonitrile copolymer (ABS), polymethylmethacrylate (PMMA), polyoxymethylene (POM), polypropylene (PP), polyamide (PA), high-density polyethylene (HDPE), or the like.

The bending portion 12 bends in a predetermined direction according to movement of an operation lever 30 provided on the operation portion 3. The operation lever 30 is a member operated by a user of the endoscope 1. A plurality of wires not shown in the drawing are inserted through the insertion portion 2, and distal ends of the plurality of wires are connected to the bending portion 12. Proximal ends of the plurality of wires are connected to a wire pulling mechanism provided in the operation portion 3.

The wire pulling mechanism changes pulling amounts of the plurality of individual wires according to the movement of the operation lever 30. A bending direction and an angle of the bending portion 12 change according to changes in the pulling amounts of the plurality of wires. A configuration of the bending portion 12 where a bending direction and an angle change according to changes in pulling amounts of a plurality of wires is a known configuration and hence, detailed description of such a configuration will be omitted.

The bending portion 12 is a columnar member having flexibility and extending in the longitudinal direction of the insertion portion 2. The bending portion 12 is formed using a second material being a thermoplastic resin. A second temperature T2 being a melting point of the second material is higher than the first temperature T1 being the melting point of the first material.

A kind of the second material is so-called engineering plastic. However, the kind of the second material is not particularly limited. It is preferable that a difference between the second temperature T2, being the melting point of the second material, and the first temperature, being the melting point of the first material, be equal to or greater than 30° C. In the present embodiment, for example, the second material may be nylon 66. In a case where the second material is nylon 66, the second temperature T2 is approximately 280° C.

A distal end 12*a* of the bending portion 12 is coupled to a proximal end portion 11*b* of the distal end forming portion 11. A space is formed in the bending portion 12 to extend in the longitudinal direction, and the plurality of wires, an electric cable connected to the image pickup apparatus, and the like are inserted through the space.

An outer peripheral surface of the bending portion 12 has a plurality of slits 12*c* with a depth direction being a direction orthogonal to the longitudinal direction. The slits 12*c* are provided to reduce bending rigidity of the bending portion 12 in a predetermined direction.

The flexible tube 13 is a tubular member having flexibility and extending in the longitudinal direction of the insertion portion 2. A distal end portion 13*a* of the flexible tube 13 is coupled to a proximal end 12*b* of the bending portion 12. That is to say, in the present embodiment, the bending portion 12 is interposed in the insertion portion 2 at a predetermined position between the distal end forming portion 11 and the flexible tube 13. Although not shown in FIG. 2, a proximal end portion of the flexible tube 13 is coupled to the operation portion 3. The plurality of wires, the electric cable connected to the image pickup apparatus, and the like are inserted through the flexible tube 13. An outer peripheral surface of the flexible tube 13 at a portion near the distal end portion 13*a* is covered by a material made of a resin.

The elastic member 14 is a tubular member that covers the bending portion 12 to maintain watertightness of the outer peripheral surface of the bending portion 12. The purpose of maintaining watertightness of the outer peripheral surface of the bending portion 12 with the elastic member 14 is to prevent infiltration of liquid or the like into the insertion portion 2 through the slit 12*c*.

The elastic member 14 is formed using a third material which is different from the first material and the second material. That is to say, the distal end forming portion 11, the bending portion 12, and the elastic member 14 of the present embodiment are respectively formed using different materials.

In the elastic member 14, an inner peripheral surface of a first end 14*a*, being one end portion, is fused to the fusion surface 11*c* of the distal end forming portion 11. The inner peripheral surface of the first end 14*a* is fused to the fusion surface 11*c* over an entire region in the circumferential direction to prevent liquid from passing through an interface.

That is to say, the third material used for forming the elastic member 14 is a thermoplastic resin, thus being fused to the first material. In the present embodiment, a third temperature T3 being a melting point of the third material is lower than the second temperature T2. In a case where the third temperature T3 takes a value between the first temperature T1 and the second temperature T2, the third temperature T3 is a value closer to the first temperature T1 than to the second temperature T2.

It is more preferable that the third temperature T3 be substantially equal to the first temperature T1. In the present embodiment, a phrase "the third temperature T3 is substantially equal to the first temperature T1" indicates that a difference between the third temperature T3 and the first temperature T1 is 10 degrees C. or less.

It is sufficient for the third material to be a material that has a melting point of the third temperature T3, that can prevent liquid from permeating through the third material, and that can form a thin pliable film. A kind of the third material is not particularly limited. In the present embodiment, for example, the third material is a polyether block amide copolymer.

In the elastic member 14, an inner peripheral surface of a second end 14*b*, being the other end portion, is fixed to an outer peripheral surface of the flexible tube 13. The inner peripheral surface of the second end 14*b* is bonded to the flexible tube 13 over an entire region in the circumferential direction to prevent liquid from passing through an interface. A method for fixing the inner peripheral surface of the second end 14*b* to the flexible tube 13 is not particularly limited. The inner peripheral surface of the second end 14*b* may be fixed to the flexible tube 13 by an adhesive agent or by fusing.

In the present embodiment, for example, the inner peripheral surface of the second end 14*b* of the elastic member 14 is bonded to the outer peripheral surface of the distal end portion 13*a* of the flexible tube 13 by fusing. The outer peripheral surface of the distal end portion 13*a* of the flexible tube 13 is covered by a fourth material being a thermoplastic resin. A fourth temperature T4 being a melting point of the fourth material is substantially equal to the first temperature T1.

As described above, the first end 14*a* of the elastic member 14 is fused to the distal end forming portion 11 provided on a distal end side of the distal end 12*a* of the bending portion 12. Further, the second end 14*b* of the elastic member 14 is fixed to the flexible tube 13 provided on a proximal end side of the proximal end 12*b* of the bending portion 12. Accordingly, the outer peripheral surface of the bending portion 12 is disposed in the space formed inside the tubular elastic member 14 having closed both ends and hence, watertightness of the outer peripheral surface of the bending portion 12 is maintained.

In the present embodiment, both the distal end forming portion 11 and the bending portion 12 are made of a resin and are coupled with each other. Therefore, when the endoscope 1 is assembled, in a fusing step where the elastic member 14 is fused to the distal end forming portion 11 by heating the elastic member 14 and the distal end forming portion 11, the bending portion 12 disposed adjacent to the distal end forming portion 11 is also heated.

If the elastic member 14 is also fused to the bending portion 12 in addition to the distal end forming portion 11 in the fusing step, the elastic member 14 obstructs deformation of the bending portion 12.

In the present embodiment, the first temperature T1 being the melting point of the fusion surface 11*c* of the distal end forming portion 11 is lower than the second temperature T2 being the melting point of the bending portion 12. Therefore, by controlling at least one of a heating temperature and a heating time period in the fusing step, the elastic member 14 can be fused to the distal end forming portion 11 while the elastic member 14 is prevented from being fused to the bending portion 12.

At least one of either the heating temperature or the heating time period in the fusing step can be easily controlled by using an electronically controlled heater. Further, work for fixing the elastic member 14 to the distal end forming portion 11 by fusing can be easily executed in a shorter time period than work adopted in a conventional endoscope where a tubular cover member is fixed by tightening a thread, for example.

The endoscope 1 of the present embodiment described above has a configuration where the distal end forming portion 11 and the bending portion 12 are formed using a resin and the elastic member 14 is fixed to the distal end forming portion 11 by fusing and hence, it is possible to reduce the number of parts and also possible to reduce man-hours required for assembly. Further, in the endoscope 1 of the present embodiment, the melting point of the distal end forming portion 11 and the melting point of the elastic member 14 are set to be lower than the melting point of the bending portion 12 and hence, in the fusing step of fixing the elastic member 14 to the distal end forming portion 11 by fusing, it is possible to easily and surely prevent the elastic member 14 from being fused to the bending portion 12. Accordingly, the endoscope 1 of the present embodiment causes no trouble in an action of the bending portion 12, and can be manufactured at low cost.

Second Embodiment

Hereinafter, a second embodiment of the present invention will be described. Hereinafter, only points which make the second embodiment different from the first embodiment will be described. Constituent elements substantially equivalent to the corresponding constituent elements in the first embodiment are given the same reference symbols, and the description of such constituent elements w-ill be omitted when appropriate.

An endoscope 1 of the present embodiment differs from the endoscope 1 of the first embodiment with respect to a configuration of a distal end forming portion 11. The distal end forming portion 11 of the present embodiment is formed by combining a plurality of members made of different materials.

Figure 3:
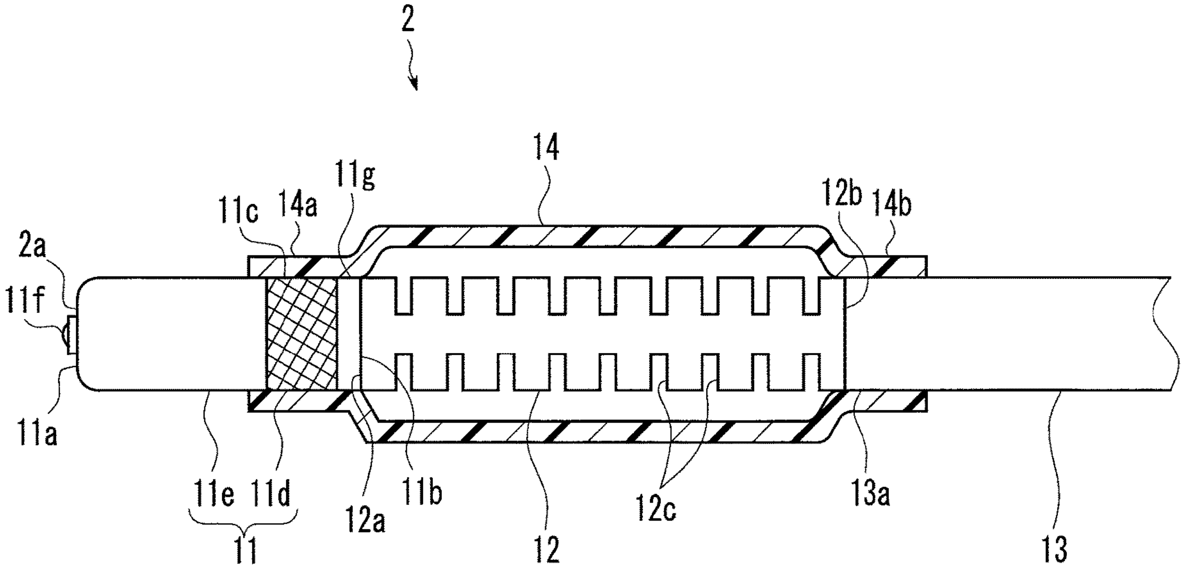
FIG. 3 is a partial cross-sectional view of an insertion portion of a second embodiment.

More specifically, as shown in FIG. 3, the distal end forming portion 11 includes an annular portion 11*d* formed using the first material and a body portion 11*e* formed using a fifth material.

The body portion 11*e* is a resin molded product formed using the fifth material being a thermoplastic resin. A fifth temperature T5 being a melting point of the fifth material is higher than the first temperature T1 being the melting point of the first material. The fifth temperature may be equal to or higher than the second temperature. As described in the first embodiment, the second temperature is the melting point of the second material used for forming the bending portion 12.

The body portion 11*e* is a columnar member extending in the longitudinal direction of the insertion portion 2 from a distal end 11*a* to the proximal end portion 11*b* of the distal end forming portion 11. In other words, the distal end 12*a* of the bending portion 12 is coupled to the body portion 11*e*. A space is formed in the body portion 11*e*, and the image pickup apparatus, illumination window and the like are held in the space.

In the present embodiment, for example, the body portion 11*e* is transparent, and a portion of the body portion 11*e* forms an optical member 11*f* forming at least a portion of an objective lens and an illumination window of an image pickup apparatus. In other words, the body portion 11*e* and the optical member 11*f* are integrally molded.

A kind of the first material and a kind of the fifth material are not particularly limited. However, in the present embodiment, for example, the first material may be a styrene butadiene acrylonitrile copolymer (ABS), and the fifth material may be polycarbonate (PC).

The annular portion 11*d* is an annular member that surrounds an entire region in the circumferential direction at a portion of an outer peripheral surface of the body portion 11*e*. The annular portion 11*d* is fixed in a state of being brought into close contact with the outer peripheral surface of the body portion 11*e*. The annular portion 11*d* is bonded to the body portion 11*e* over an entire region in the circumferential direction to prevent liquid from passing through an interface. In FIG. 3, for clarity, a surface of the annular portion 11*d* is cross-hatched. However, this cross-hatching is not showing the annular portion 11*d* in cross section.

A method for fixing the annular portion 11*d* to the body portion 11*e* is not particularly limited. In the present embodiment, for example, the annular portion 11*d* and the body portion 11*e* are molded by two-color molding, thus being fixed to each other. A configuration may be adopted where the annular portion 11*d* is fixed to the body portion 11*e* by adhesion or by press-fitting.

An outer peripheral surface of the annular portion 11*d* forms the fusion surface 11*c*. In other words, the inner peripheral surface of the first end 14*a* of the elastic member 14 is fused to the outer peripheral surface of the annular portion 11*d*.

In the present embodiment, the body portion 11*e* includes a wall portion 11*g* at a position closer to a proximal end portion 11*b* side than the annular portion 11*d*. The wall portion 11*g* is exposed on an outer side in the circumferential direction of the distal end forming portion 11. An outer peripheral surface of the wall portion 11*g* is on the same plane as the outer peripheral surface of the annular portion 11*d*. In other words, the outer peripheral surface of the wall portion 11*g* is on the same plane as the fusion surface 11*c*.

As described above, in the endoscope 1 of the present embodiment, a portion of an outer surface of the distal end forming portion 11 is formed from the fusion surface 11*c*, which is formed using the first material, and the body portion 11*e*, being another portion of the distal end forming portion 11, is formed using the fifth material having a higher melting point than the first material.

When the endoscope 1 is assembled, in the fusing step of fusing the elastic member 14 to the fusion surface 11*c* by heating the elastic member 14 and the fusion surface 11*c*, heat is also transferred to the body portion 11*e* formed using a thermoplastic resin. However, the body portion 11*e* has a higher melting point than the elastic member 14 and the fusion surface 11*c* and hence, it is possible to surely prevent occurrence of distortion of the body portion 11*e* caused by heating in the fusing step.

Preventing occurrence of distortion of the body portion 11*e* contributes to improvement in positioning accuracy of the image pickup apparatus, for example. Therefore, such a configuration is preferable. In a case where the body portion 11*e* and the optical member 11*f* are integrally molded as in the case of the present embodiment, preventing occurrence of distortion of the body portion 11*e* contributes to exhibition of desired optical performance in picking up an image or in illumination. Therefore, such a configuration is preferable.

In the present embodiment, on the outer surface of the distal end forming portion 11, the wall portion 11*g* being a second portion is disposed at a first portion located on the proximal end portion 11*b* side of the fusion surface 11*c*, the second portion having a higher melting point than the fusion surface 11*c*. By providing the wall portion 11*g*, it is possible to prevent a portion of the annular portion 11*d* softened by heating in the fusing step from flowing out to a periphery of the bending portion 12. If a portion of the annular portion 11*d* flows out to the periphery of the bending portion 12 in the fusing step, interference may occur in a deformation action of the bending portion 12. However, in the present embodiment, it is possible to prevent occurrence of such a situation.

Other components of the endoscope 1 of the present embodiment are substantially equivalent to the corresponding components of the first embodiment. Accordingly, the endoscope 1 of the present embodiment has a configuration where the distal end forming portion 11 and the bending portion 12 are formed using a resin and the elastic member 14 is fixed to the distal end forming portion 11 by fusing and hence, it is possible to reduce the number of parts and also possible to reduce man-hours required for assembly. Further, in the endoscope 1 of the present embodiment, the melting point of the fusion surface 11*c* of the distal end forming portion 11 and the melting point of the elastic member 14 are set to be lower than the melting point of the bending portion 12 and hence, in the fusing step of fixing the elastic member 14 to the distal end forming portion 11 by fusing, it is possible to easily and surely prevent the elastic member 14 from being fused to the bending portion 12. Accordingly, the endoscope 1 of the present embodiment causes no interference in the action of the bending portion 12, and can be manufactured at low cost.

Third Embodiment

Hereinafter, a third embodiment of the present invention will be described. Hereinafter, only points which make the third embodiment different from the first embodiment will be described. Constituent elements substantially equivalent to the corresponding constituent elements in the first embodiment are given the same reference symbols, and the description of such constituent elements will be omitted when appropriate.

Figure 4:
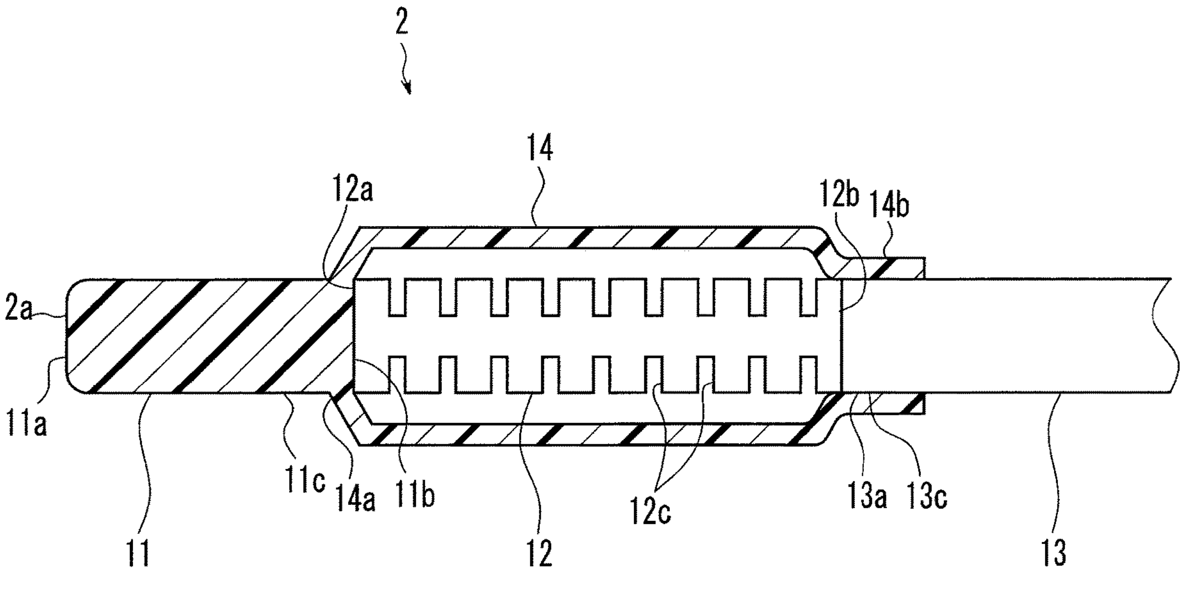
FIG. 4 is a partial cross-sectional view of an insertion portion of a third embodiment.

As shown in FIG. 4, an elastic member 14 of the present embodiment is integrally molded with the distal end forming portion 11. That is to say, the first end 14*a* of the elastic member 14 having an annular shape is integrally formed with the outer peripheral surface of the distal end forming portion 11.

A fusion surface 13*c* is provided on the outer peripheral surface of the distal end portion 13*a* of the flexible tube 13. The fusion surface 13*c* is formed using the fourth material being a thermoplastic resin. The fourth temperature T4 being the melting point of the fourth material is substantially equal to the first temperature T1. The second end 14*b* of the elastic member 14 is bonded, by fusing, to the fusion surface 13*c* provided on the flexible tube 13.

In the present embodiment, the first end 14*a* of the elastic member 14 is integrally molded with the distal end forming portion 11 provided on the distal end side of the distal end 12*a* of the bending portion 12. Further, the second end 14*b* of the elastic member 14 is fused to the flexible tube 13 provided on the proximal end side of the proximal end 12*b* of the bending portion 12. Accordingly, the outer peripheral surface of the bending portion 12 is disposed in the space formed inside the tubular elastic member 14 having closed both ends and hence, watertightness of the outer peripheral surface of the bending portion 12 is maintained.

Other components of the endoscope 1 of the present embodiment are substantially equivalent to the corresponding components of the first embodiment. Accordingly, the endoscope 1 of the present embodiment has a configuration where the distal end forming portion 11 and the elastic member 14 are integrally molded using a resin and the end portion of the elastic member 14 is fixed to the flexible tube 13 by fusing and hence, it is possible to reduce the number of parts and also possible to reduce man-hours required for assembly. Further, in the endoscope 1 of the present embodiment, the melting point of the fusion surface 13*c* of the flexible tube 13 and the melting point of the elastic member 14 are set to be lower than the melting point of the bending portion 12 and hence, in the fusing step of fixing the elastic member 14 to the flexible tube 13 by fusing, it is possible to easily and surely prevent the elastic member 14 from being fused to the bending portion 12. Accordingly, the endoscope 1 of the present embodiment causes no interference in the action of the bending portion 12, and can be manufactured at low cost.

The present invention is not limited to the embodiments described above, and can be suitably changed without departing from the gist or concept of the invention which can be read in the claims and in the entire description. Endoscopes with such changes also fall within the technical scope of the present invention.

What is claimed is:

1. An insertion portion for use with an endoscope, the insertion portion comprising:

a distal end portion comprising:

a first component having a first fusion surface formed of a first resin material, the first resin material having a melting point of a first temperature; and a second component formed of a second resin material, the second resin material being transparent;

a bending portion formed of a material having a melting point of a second temperature higher than the first temperature, the bending portion having a unitary body having a plurality of slits arranged longitudinally in a predetermined direction so as to be bendable in the predetermined direction; and an elastic tube formed of a third resin material different from the first resin material and different from the second resin material, the elastic tube configured to cover the bending portion, an end portion of the elastic tube being heat fused to the first fusion surface, wherein the second component is integrally formed as an optical member comprising at least a portion of a lens and an illumination window.

2. The insertion portion according to claim 1, wherein the elastic tube has a melting point of a third temperature, and a temperature difference between the third temperature and the first temperature is 10° C. or less.

3. The insertion portion according to claim 1, wherein the material of the bending portion is a resin material having the second temperature, and a temperature difference between the first temperature and the second temperature is equal to or greater than 30° C.

4. The insertion portion according to claim 1, wherein the distal end portion is coupled to a distal end side of the bending portion.

5. The insertion portion according to claim 4, wherein the first component is proximal relative to the second component and, the second component having a melting point higher than the first temperature.

6. The insertion portion according to claim 1, further comprising a flexible tube coupled to a proximal end side of the bending portion;

wherein the flexible tube comprising a third component formed at a distal end portion of the flexible tube.

7. The insertion portion according to claim 6, wherein an outer peripheral surface of the third component is covered by a fourth resin material, and the fourth resin material forms a second fusion surface.

8. The insertion portion according to claim 7, wherein the fourth resin material has a melting point of a fourth temperature, and a temperature difference between the fourth temperature and the first temperature is equal to or less than 10° C.

9. The insertion portion according to claim 1, wherein the elastic tube being heat fused to the first fusion surface is configured to be heat fused only on an outside of a circumferential surface of the bending portion.

10. The insertion portion according to claim 1, wherein a distal end of the bending portion is connected to a proximal end of the first fusion surface.

11. An endoscope comprising:

the insertion portion according to claim 1, the insertion portion further comprising:

a flexible tube provided proximally relative to the bending portion, the flexible tube having a second fusion surface; and the distal end portion is provided distally relative to the bending portion;

wherein the elastic tube has a distal end and a proximal end;

the proximal end of the elastic tube is heat fused to the second fusion surface.

12. An insertion portion for use with an endoscope, the insertion portion comprising:

a distal end portion comprising:

a first component having a first fusion surface formed of a first resin material having a melting point of a first temperature; and a second component formed of a second resin material, the second resin material being transparent;

a bending portion formed of a material having a melting point of a second temperature higher than the first temperature, the bending portion having a unitary body having a plurality of slits arranged longitudinally in a predetermined direction so as to be bendable in the predetermined direction, the bending portion being continuously provided on a proximal end side of the distal end portion;

an elastic tube covering the bending portion, the elastic tube formed of a third resin material different from the first resin material and having a melting point of a third temperature, an end portion of the elastic tube being heat fused to the distal end portion; and a flexible tube continuously provided on a proximal end side of the bending portion, wherein the second component is integrally formed as an optical member comprising at least a portion of a lens and an illumination window.

13. The insertion portion of the endoscope according to claim 12, wherein a temperature difference between the third temperature and the first temperature is equal to or less than 10° C.

14. The insertion portion of the endoscope according to claim 12, wherein the material of the bending portion is a resin material having the second temperature, and a difference between the first temperature and the second temperature is equal to or greater than 30° C.

15. The insertion portion of the endoscope according to claim 12, wherein the first resin material is selected from a group consisting of polycarbonate, a styrene butadiene acrylonitrile copolymer, polymethylmethacrylate, polyoxymethylene, polypropylene, polyamide, and high-density polyethylene.

16. The insertion portion of the endoscope according to claim 12, wherein the material having the melting point of the second temperature is nylon 66.

17. The insertion portion of the endoscope according to claim 12, wherein the second third resin material is a polyether block amide copolymer.

18. A method for manufacturing an insertion portion of an endoscope, the method comprising:

forming a first component of a distal end portion from a first resin material, the first component having a fusion surface having a melting point of a first temperature and forming a second component of the distal end portion from a transparent second resin material;

forming a bending portion using a material having a melting point of a second temperature higher than the first temperature, the bending portion having a unitary body having a plurality of slits arranged longitudinally in a predetermined direction so as to be bendable in the predetermined direction, and causing the bending portion to be continuously provided on a proximal end side of the distal end portion;

causing a flexible tube to be continuously provided on a proximal end side of the bending portion;

forming an elastic tube having a first end and a second end; and heat fusing the first end of the elastic tube to the fusion surface of the distal end portion, the elastic tube being formed using a third resin material having a melting point of a third temperature and being different from the first resin material, wherein the second component is integrally formed as an optical member comprising at least a portion of a lens and an illumination window of the endoscope.

19. The method for manufacturing the insertion portion of the endoscope according to claim 18, wherein the second end of the elastic tube is fixed to the flexible tube.

* * * * *